(12) United States Patent
Sanders

(10) Patent No.: US 11,547,651 B2
(45) Date of Patent: Jan. 10, 2023

(54) ECOFRIENDLY BIOFILM-DISRUPTING ANTIMICROBIAL FORMULATIONS, THEIR DEVELOPMENT, AND THEIR USES

(71) Applicant: Alira Health Boston LLC, Framingham, MA (US)

(72) Inventor: Mitchell Corey Sanders, Grafton, MA (US)

(73) Assignee: Alira Health Boston LLC, Framingham, MA (US)

( * ) Notice: Subject to any disclaimer, the term of this patent is extended or adjusted under 35 U.S.C. 154(b) by 0 days.

(21) Appl. No.: 16/550,122

(22) Filed: Aug. 23, 2019

(65) Prior Publication Data

US 2020/0121582 A1  Apr. 23, 2020

Related U.S. Application Data

(63) Continuation of application No. PCT/US2018/019400, filed on Feb. 23, 2018.

(60) Provisional application No. 62/462,686, filed on Feb. 23, 2017.

(51) Int. Cl.
| | |
|---|---|
| *A61K 8/11* | (2006.01) |
| *A61K 8/18* | (2006.01) |
| *A61Q 11/00* | (2006.01) |
| *A61Q 19/00* | (2006.01) |
| *A61K 8/73* | (2006.01) |
| *A61K 8/87* | (2006.01) |
| *A61K 47/34* | (2017.01) |
| *A61K 47/36* | (2006.01) |
| *A61K 47/38* | (2006.01) |
| *A61Q 19/10* | (2006.01) |

(52) U.S. Cl.
CPC ............. *A61K 8/73* (2013.01); *A61K 8/731* (2013.01); *A61K 8/733* (2013.01); *A61K 8/87* (2013.01); *A61K 47/34* (2013.01); *A61K 47/36* (2013.01); *A61K 47/38* (2013.01); *A61Q 11/00* (2013.01); *A61Q 19/10* (2013.01)

(58) Field of Classification Search
None
See application file for complete search history.

(56) References Cited

U.S. PATENT DOCUMENTS

| | | | |
|---|---|---|---|
| 4,944,947 A | 7/1990 | Newman | |
| 5,051,304 A * | 9/1991 | David | A61K 8/737 428/402.2 |
| 5,720,949 A | 2/1998 | Davis | |
| 2006/0105000 A1* | 5/2006 | Friedman | A61K 9/0053 424/400 |
| 2007/0134171 A1 | 6/2007 | Dodds et al. | |
| 2015/0328087 A1* | 11/2015 | Choi | A61K 8/19 424/195.17 |
| 2015/0374634 A1* | 12/2015 | Koo | A61K 9/5026 424/451 |
| 2016/0000094 A1* | 1/2016 | Modak | A61K 8/9789 424/736 |
| 2017/0027168 A1 | 2/2017 | Heath | |

FOREIGN PATENT DOCUMENTS

| | | | | |
|---|---|---|---|---|
| EP | 1030734 A1 * | 8/2000 | | A61K 8/731 |
| EP | 1030734 B1 | 8/2003 | | |

OTHER PUBLICATIONS

International Preliminary Report on Patentability and the Written Opinion of the International Searching Authority dated Aug. 27, 2019 for PCT/US2018/019400.
International Search Report and Written Opinion of the International Searching Authority dated Jul. 31, 2018 for PCT/US2018/19400.

* cited by examiner

*Primary Examiner* — Brian Gulledge
(74) *Attorney, Agent, or Firm* — Prince Lobel Tye LLP; Brian M. Dingman

(57) ABSTRACT

A skin care, wound care, or oral care device, comprising an essential oil stabilized into a polymerizable substance.

15 Claims, No Drawings

ECOFRIENDLY BIOFILM-DISRUPTING ANTIMICROBIAL FORMULATIONS, THEIR DEVELOPMENT, AND THEIR USES

CROSS-REFERENCE TO RELATED APPLICATIONS

This application is a continuation of and claims priority to PCT/US2018/019400 filed on 23 Feb. 2018, which itself claimed priority of Provisional Application No. 62/462,686 filed on 23 Feb. 2017.

BACKGROUND

This disclosure relates to antimicrobial formulations.

Many antimicrobial formulations that are currently used in the wound care, skin, cosmetics, and the oral care industries include antimicrobial substances that are toxic to the environment, are not directed broad spectrum, and have questionable long-term status within the European Union and with the Food and Drug Administration (FDA).

In the oral care and skin industry one of the common antimicrobial ingredients is Triclosan (5-Chloro-2-(2,4-dichlorophenoxy)phenol). Triclosan is now in a variety of consumer products including toothpastes, soaps, deodorants, fabrics, and toys. Triclosan is a modest antimicrobial with a microbial inhibitory concentration (MIC) of 125 µg/ml but has major concerns over its potential negative impact on the environment due to its high toxicity to aquatic animal and plant species including but not limited to algae, fish, sea urchins and other invertebrates. Based on the ecotoxicology database (ECOTOX) hosted by the US Environmental Protection Agency, Triclosan has 513 records of being unsafe for the aquatic environment. Although relatively safe for humans, the compound has a $LD_{50}$ in mice of 1.5 mg/day.

In the wound, skin, and to a lesser extent the oral care industry, silver is a commonly used antimicrobial. Silver formulations are the major antimicrobial used in advanced wound dressings and rinse solutions for chronic wounds (diabetic foot ulcers, venous leg ulcers and pressure ulcers) that are prone to infection. Silver comes in many chemical forms, including but not limited to silver chloride ($AgCl_2$), silver sulfadiazine ($C_{10}H_9AgN_4O_2S$), silver nitrate ($AgNo_3$), and several forms of nano crystalline silver. Silver has a respectable MIC of 7.5 µg/ml but may cause skin and eye discoloration. Not unlike Triclosan, there is a concern over silver resistance and the serious concern that silver is unfriendly to aquatic life with 5,266 records on the ECOTOX Database. Many countries in Europe have reduced the use of silver in advanced wound care and the trend is to either develop passive materials that can remove bacteria biofilms or search for new broad-spectrum antimicrobials that are safe for the environment.

SUMMARY

Here we report the development of ecofriendly antimicrobial formulations that have been optimized to disrupt bacterial biofilms and are safe for human use and the environment.

Antimicrobial compounds that are able to disrupt bacterial biofilms better than nanocrystalline silver but are more ecofriendly and are safe for human use. In vitro studies suggest that these compounds can have a dual role of having a fresh clean scent while still being highly selective for bacterial biofilms common in skin, wound, and oral care. We have developed these ecofriendly antimicrobials into nano and microcrystalline particles that can accomplish an extended release, for up to 30 days. These novel microcrystalline formulations of cinnamon, lemongrass, and to a lesser extent peppermint are highly effective broad spectrum antimicrobial agents that will reduce bacterial biofilms in skin, wound, and oral infections, while reducing unwanted odors.

Based on an exhaustive literature search for antimicrobial compounds from research papers and patent databases, we developed a list of over 48 potential antimicrobial compounds that are used in skin care, wounds, oral care, and cosmetics. Each of these compounds has been shown to be antimicrobial but many of them have limited effectiveness against multiple bacterial species and are non-ecofriendly. The list includes: 1) QAC (benzalkonium chloride), 2) PHMB, 3) carboxymethyl chitosan, 4) ethyl lauryl arginate, 5) hydrogen peroxide, 6) jojoba oil, 7) lemongrass (nerol, geranial and geraniol), 8) magnilol, 9) manuka honey, 10) octenidine, 11) piper betel (pepper leaves), 12) attacincoleoptericin, 13) lauric acid, 14) polyhexanide, 15) cetylpyridinium chloride, 16) chlorhexidine gluconate, 17) cinnamon, 18) peppermint oil, 19) polyDADMAC, 20) polymyxin B sulfate, 21) aloesin, 23) coriander, 24) cumin oil, 25) mint, 26) mustard oil, 27) silver, 28) zeolite, silver, 29) zinc ascorbyl phosphate, 30) benzoyl peroxide, 31) allicin (garlic), 32) thymol, 33) zinc oxide and chitosan, 34) coconut oil, 35) witch hazel, 36) chlorine dioxide, 37) hypochlorous acid, 38) methyl salicilate (Winter Green oil), 39) methylparaben, 40) PVP Iodine, 41) sanguinarine, 42) selenium, 43) zinc oxide, 44) chitosan, 45) Triclosan, 46) curculigo orchioides (golden eye-grass), 47) nitro substituted salicylic acid, and 48) hydroxy-alkyl maleimides.

Many of these compounds have questionable or uncharacterized broad spectrum antimicrobial activities, are not safe for humans, and/or are not environmentally friendly.

JMP® SAS is a powerful software package for multivariate analysis of drug formulations and can provide powerful insights into exploratory data analysis (EDA) that has led to our discovery of novel ecofriendly antimicrobial formulations.

We used a multivariate analysis approach JMP® SAS software to analyze the top 48 antimicrobial compounds listed above, to compare their antibacterial activities with human safety based on the National Institute of Health (NIH) toxicology data network of hazardous substance databank (Toxnet HSDB), Eco-friendliness based on ECOTOX, and the opinion of European Union as to the acceptable use of the antimicrobial based EU Directives (ECHA Article 95 and Annex 95).

All examples and features mentioned below can be combined in any technically possible way.

In one aspect, a skin care, wound care, or oral care device includes an essential oil stabilized into a polymerizable substance. Stabilization can include, but is not limited to, crystallization, tight packing, ordering, condensing, concentrating, precipitating, and saturating; non-limiting examples are given below. The essential oil can be micro-crystallized or microencapsulated before it is stabilized into the polymerizable substance. The essential oil can be microencapsulated into pectin. The microencapsulation can take place in a 1-10% pectin solution. The polymerizable substance can comprise an alginate polymer. The polymerizable substance can comprise a polyurethane foam. The polymerizable substance can comprise cellulose. The cellulose can comprise nanocrystalline or microcrystalline cellulose particles.

The polymerizable substance can comprise microcellulose, nanocellulose, alginate, polyurethane, collagen, hyaluronic acid, PEG, silicone, or a silicone acrylic polymer.

The essential oil can be mixed in to a polymeric material comprising silicone, acrylic, nylon, polylactic acid, polyethylene, polypropylene, Teflon, polystyrene, polyurethane, alginate, PET, or PEEK. The oral care device can comprise a rinse, mouthwash, dental floss, or toothbrush, or toothpaste. The wound care device can comprise a rinse, gel, foam, wound dressing, suture, staple, or wipe. The skin care device can be a rinse, shampoo, wipe, or mask. The essential oil may inhibit dental caries, bad breath, gingivitis, or periodontal disease. The essential oil may inhibit acne, dandruff, psoriasis, body odor, and athlete's foot.

DETAILED DESCRIPTION

For the JMP® SAS analysis we rated the human safety based on the Toxnet HSDB database. We ranked the safety using the following point scale: 5) Safe, 4) minor irritation, 3) moderate, 2) high risk, 1) unacceptable, and "ND" for not determined. About 20% of the compounds had a high risk to human safety from acute significant toxicities including skin irritation, laryngeal & pulmonary irritation, atrial fibrillation, muscle pain, cooling sensation, and burning sensations.

The MIC of the antimicrobials was from literature review as well as in vitro studies in our lab with the five major oral care and five major wound care pathogens. In the literature typically only one bacteria was tested, thus, it was difficult to ascertain whether the target was a broad spectrum antimicrobial. Oral care pathogens tested include: *Fusobacterium nucleatum* ss *vincentii, Porphyromonas gingivalis, Prevotella intermedia, Aggregatibacter actinomycetemcomitans* and *Streptococcus mutans*. Wound care pathogens included: *Pseudomonas aeruginosa, Streptococcus pyogenes, Staphylococcus aureus, Enterococcus faecalis,* and *Proteus mirabilis*. For the JMP® SAS analysis the antimicrobial scoring was based on the MIC in µg/ml using the following point scale: 5) 1-10 µg/ml, 4) 11-25 µg/ml, 3) 26-50 µg/ml, 2) 51-100 µg/ml, 1) >101, and ND for not determined.

Eco-friendliness ratings were based on the number of references from the ECOTOX database. The scoring used the following point scale: 5) no toxicity to aquatic and terrestrial organisms, 4) 1-10 result records, 3) 11-25, 2) 26-50, 1) >51, and ND for not determined. Commonly used compounds such as Triclosan and silver were given an unacceptable Ecofriendly score of 1. Other essential oils such as cinnamon, pepper, magnolia, and lemongrass were very ecofriendly but surprisingly had quite acceptable MICs.

Since the European Union seems to be more stringent than the USA in terms of examining the safety of antimicrobial formulations we wanted to examine to see if any of these compounds were listed in the ECHA Article 95 and Annex 95 directives. We scored the compounds as a 5) if they were listed as acceptable for use and 3) if they were either not listed or determined to be unacceptable.

Based on the multivariate analysis using JMP® SAS of the antimicrobial targets we were able to separate the targets based on total combined score for the five variables (antimicrobial activity, eco-friendliness, safety, ECHA approval, and Annex 5 approval, as described above). The top scorers (the most desirable) targets include: QAC (benzalkonium chloride), PHMB, carboxymethyl chitosan, ethyl lauryl arginate, hydrogen peroxide, jojoba oil, lemongrass (nerol, geranial and geraniol), magnilol, manuka honey, octenidine, piper betel (pepper leaves), attacin-coleoptericin, lauric acid, polyhexanide, cetylpyridinium chloride, chlorhexidine gluconate, cinnamon, peppermint oil, polyDADMAC, and polymyxin B sulfate, In contrast targets with the lowest combined scores were considered to be the least desirable. Least desirable targets include: thymol, zinc oxide and chitosan, coconut oil, nanosilver, witch hazel, chlorine dioxide, hypochlorous acid, methyl salicilate (Winter Green oil), methylparaben, PVP Iodine, sanguinarine, selenium, zinc oxide nano particles, chitosan, Triclosan, curculigo orchioides (golden eyegrass), nitro substituted salicylic acid, and hydroxy-alkyl maleimides Broad Spectrum In order to directly compare the top potential Ecofriendly antimicrobial candidates from the JMP SAS multivariate analysis described above, we examined how some of these compounds (aloesin, zinc pyrithione, cinnamon, lemongrass, manuka honey, peppermint, jojoba oil) performed against common oral care and wound care pathogens, using silver as a positive control. Silver is a broad spectrum with a 5-fold log reduction of most bacterial pathogens with planktonic bacterial and bacterial biofilms. If an ecofriendly antimicrobial is going to have any utility it needs be able to be more effective than silver at killing the common oral care and wound care pathogens. Our in vitro data indicates that only three compounds have broad spectrum antimicrobial activities better than silver: cinnamon, lemongrass, and zinc pyrithione. Compounds such as jojoba, Manuka honey, and aloesin are reported to have antimicrobial activity, but in our independent studies we found that these compounds were inferior to silver and thus were excluded from further consideration. Zinc pyrithione is commonly used as an antibacterial and antifungal, is safe for human use, and is a common ingredient in dandruff shampoo. However, we excluded zinc pyrithione from further consideration because it has a rather poor ecotoxicology score of 1 (see our scoring system above) with 151 references in the ecotoxicology database.

Essential oils of cinnamon and lemongrass can be incorporated into medical devices (oral, skin, or wound care) without further modification. Essential oils of cinnamon and lemongrass can also be microcrystallized alone or microencapsulated in combination with a polymeric carrier (e.g. a microalginate, microcellulose, hydrogels, pectin, or collagen) to form combination products that are able to have an extended release of antimicrobials for up to 30 days.

The crystallization and encapsulation of these ecofriendly antimicrobials (cinnamon and lemongrass) can result in the extended release of antimicrobial for up to 30 days.

Microcrystallization of Essential Oils

Crystallization of essential oils can be performed similar to methods provided for protein and DNA molecules with the modification of using agents to encourage nucleation of the essential oil as described by Landau et al (1997) for hydrophobic proteins. Nucleating reagents include detergents, precipitants, and other additives. Detergents used in the essential oil microcrystallization include but are non-limited to nonionic detergents such as HECAMEG, CHAPS, MEGA 8, MEGA 10, and Tween 20 and Tween 80 at concentration of 0.1-10% in the crystallization matrix. Salt used to accelerate crystallization include 10 mM-0.5 M ammonium sulfate.

Microencapsulation

Cinnamon and lemongrass essential oils were microencapsulated into 1-4% pectin as described below. A 25 ml solution of 1-10% pectin was brought to a boil 1-2 minutes to dissolve the pectin granules and then allowed to cool to room temperature (25° C.) prior to use. One ml of the essential oil was then mixed with the 25 ml of room temperature pectin and then the solution was vortexed for 30 seconds to allow for the encapsulation of the ecofriendly antimicrobials into the pectin shell. In the encapsulated cinnamon oil, there are large spheres of pectin, and a small number (1-3) entrapped small spheres inside the large spheres which are the ecofriendly antimicrobials. After standing for 10-30 min the pectin encapsulated oils can be separated from the remaining mixture by pipetting to remove the bottom layer.

The microencapsulated pectin can then be further polymerized into a polymeric structure such as alginate, silicone, collagen, hydrogels, or polyurethane to create an antimicrobial wound dressing.

Alginate Wound Dressings

Sodium alginate was dissolved into distilled water to produce alginate solutions with concentration of 0.5-4%. The solutions were left standing for at least 24 hours to disengage bubbles before use. Afterwards, sodium alginate solution (30-100 ml) and pectin encapsulated ecofriendly antimicrobials (1-10 ml) were homogenized by vortexing for 30 seconds and then layered onto a carrier bandage saturated with 4% calcium chloride to polymerize the antimicrobial into the alginate polymer. After 4 hours, the alginate dressing is fully polymerized and can be sealed into a clear plastic pouch to maintain the moisture of the alginate dressing which can be processed by gamma or ethylene oxide, or E beam sterilization.

Polyurethane Foam Wound Dressing

Alternatively, the ecofriendly antimicrobials can be polymerized into a polyurethane foam dressing during the curing process as described below. Briefly, 1.6 ml of Part A polyurethane was mixed with 1.2 ml of Part B polyurethane, 5-100 µl of a silane (to promote open cell formation in the polyurethane), and 10-100 µl of the pectin encapsulated essential oils and then quickly pipetted into a dressing mold to allow for overnight curing. In the preferred embodiment the silane used was N-(2-Aminoethyl)-3-aminopropyl silane. However other silanes or detergents could be used to make an open cell structure in the polyurethane.

Microencapsulation into Cellulose

Another example of a polymeric micro carrier is the use micro and nanocrystalline cellulose. Micro- and nanocrystalline cellulose particles were prepared through a modified acid hydrolysis procedure by the method of Ahmadi et al, (2014). For preparation of nanocrystalline cellulose particles, 2 g of cut filter paper was hydrolyzed with 1 M sulfuric acid or hydrochloric acid at 45° C. for 75 min under continuous stirring at 200 rpm. The cellulose hydrolysate was centrifuged 16000×g for 10 min, and the precipitate was neutralized with an equal volume of 1 M NaOH. The precipitate was rinsed 5× with distilled water and then loaded with 0.1-10% essential oils. For the formation of microcrystalline particles, the cellulose was acid washed for only five minutes and then neutralized with. NaOH, rinsed, and loaded with essential oils, as described above. In some instances, the micro and nanocrystalline loaded cinnamon and lemongrass were cross linked with 1-10 mM calcium chloride ($CaCl_2$) for 10 min-2 hours. Crosslinking improves the extended release characteristic of the ecofriendly antimicrobials for up to 30 days.

Alternatively, the antimicrobial could be polymerized into other polymeric substances to generate antimicrobial device combination products. Other examples of polymeric materials include but are not limited to acrylic, nylon, polylactic acid, polyethylene, polypropylene, Teflon, polystyrene, polyurethane, alginate, polyethylene terephthalate (PET), polyether ether ketone (PEEK), and 2, 2'-azinobis-(3ethybenzthiazoline sulfonic acid (ABTS). One example is to copolymerize the ecofriendly antimicrobials into the bristles of a toothbrush for the extended release of antimicrobials to inhibit gingivitis, dental caries, and periodontal disease.

In another embodiment the ecofriendly antimicrobials are polymerized into a medical device for oral care, wound care, or skin care. Many adhesives used in wound care include silicone, acrylic, or a combination thereof. We have copolymerized cinnamon and lemongrass oil into the silicone during the curing process. Briefly cinnamon was mixed with silicone at a final concentration of 1-50% and then was poured into a mold to cure overnight at room temperature. Alternatively, the silicone can be cured in a few minutes with a high intensity UV light.

Our findings indicate that the alginate is better at eluting the antimicrobials based on the zone of inhibition studies with *Staphylococcus aureus* and *Candida albicans*. Briefly, $10^7$ colony forming units (CFU) of *Staphylococcus aureus* bacteria, or $10^7$ of *Candida albicans*, was plated onto a blood agar plate and a small 10 mm polymeric material (alginate) was impregnated with 1%-4% cinnamon or lemongrass was placed on top of the plate and the plate was incubated for 37° C. for overnight. In the morning the plate was observed for a zone of inhibition from the ecofriendly antimicrobial leaching from the polymeric material. For cinnamon and lemon grass the zone of inhibition (ZOI) for *C. albicans* was similar (~10-12 mm) but for *S. aureus* the lemongrass outperformed cinnamon and had a greater ZOI of 20 mm vs. 10 mm for cinnamon.

Polymerization in UV Curable Hydrogels

In yet another embodiment the essential oil of cinnamon or lemongrass alone or mixed 1:1 with Aloe Vera and then following mixing combined with premixed thiol modified hyaluronic acid and gelatin that is crosslinked with PEG nonborene (tripentaerythritol) and then crosslinked for 30 min with a 365 nm light source. The liquid hydrogel can be cast in a mold or 3D printed in a syringe with a fine bore tip and then UV cured in layers to provide for a reticulating pattern that can draw exudate away from the wound bed.

Toothpastes and Mouthwashes

Toothpastes and mouthwashes have a number of common ingredients that include antimicrobials, abrasives, detergents, flavorants, and humectants. Tables 1 and 2 show the range minimum and maximum ingredient concentrations for some of the common toothpaste and mouthwash ingredients that may be but need not be in our formulations. Also, these ranges are illustrative but not limiting of the formulations. In the present disclosure, active concentrations of cinnamon and lemongrass sufficient for antimicrobial activity (at a concentration of from about 0.001% to about 0.1%) are used; the essential oils are not simply used at very low concentrations as minor flavorants as they are in other products. Some of the less common ingredients are also listed in each table.

Table 1 sets out the formulation of a toothpaste with ecofriendly ingredients. We used Jump SAS (reviewing patents and commercial product information) to map the range of concentrations of the major toothpaste ingredients. The major ingredients are shown in table 1. Other less common ingredients include: phosphoric acid, sorbitan monoisostearate, colloidal silica, stronium EDTA, chalk, PEG 32, VEEGUM HV, TSPP, TMP, silica zeodent, 70 PVP/VA, PEG 6, NA bicarbonate, Polyaxamer 47, Na tripolyphosphate, urea peroxide, Tecosil, peroxide ($H_2O_2$), Permulen, TR2, Cocoamido-Haxametaphosphate, Cetyl alcohol, and Stearyl alcohol.

TABLE 1

Toothpaste Ingredients

|  | Min % | Max % |
|---|---|---|
| Ecofriendly antimicrobials | 0.001 | 0.1 |
| 1 Sodium hydroxide | 0.58 | 58 |
| 2 Calcium carbonate or sodium carbonate | 0.5 | 53.5 |
| 3 Calcium Pyrophosphate or Dicalcium phosphate dihydrate | 8.1 | 52.5 |
| 4 FGNC | 40 | 50 |
| 5 Stannous Fluoride | 0 | 40 |
| 6 Water | 5.8 | 34 |
| 7 Silica Abrasive (HSC DP105) | 4.6 | 32 |
| 8 Glycerine | 8 | 30 |
| 9 Other Ingredients | 0 | 22 |
| 10 PEG 1500 or PEG 6000 | 13 | 10 |
| 11 Thickening Silica | 1 | 9.25 |
| 12 Sodium Alkyl Sulfate (28.8%) | 2.3 | 6 |
| 13 Sodium lauryl sulfate (SLS) | 0.7 | 5.71 |
| 14 60/40 PVP/VA | 1 | 5 |
| 15 Sodium Carboxymethyl Cellulose | 0.5 | 4 |
| 16 MFIL | 1.5 | 3.75 |
| 17 Sodium Silicate | 1.75 | 3.5 |
| 18 Monosodium Orthophosphate Monohydrate | 0.3 | 2.15 |
| 19 Carbopol 956 | 0.3 | 2 |
| 20 GANTREZ S97 | 0.3 | 2 |
| 21 Trisodium Phosphate | 1.5 | 1.5 |
| 22 Tribasic Sodium Phosphate Dodecahydrate | 1.1 | 1.1 |
| 23 Sodium gluconate | 1 | 1.06 |
| 24 Sodium Carrageenan or Sodium Alginate | 0.04 | 1 |
| 25 Titanium Dioxide | 0.5 | 1 |
| 26 Sodium coconut monoglyceride sulfonate | 0.7 | 0.9 |
| 27 Phytic Acid 50% | 0.8 | 0.8 |
| 28 Zinc citrate dihydrate | 0.53 | 0.53 |
| 29 Saccharin, Sucralose, | 0.12 | 0.5 |
| 30 sodium phosphate | 0.42 | 0.5 |
| 31 hydroxyethyl cellulose | 0.5 | 0.5 |
| 32 HCL Stannous Gluconate (A: 33.75, B: 31.6) | 0.5 | 0.43 |
| 33 Magnesium Aluminum silicate | 0.3 | 0.4 |
| 34 Stannous Chloride Dihydrate | 0.1 | 0.16 |
| 35 Sodium monofluorophosphate | 1 | 0.1 |
| 36 Color | 0.003 | 0.047 |

Table 2 sets out a formulation for an ecofriendly mouthwash or rinse. We used Jump SAS (reviewing patents and commercial product information) to map the range of concentrations of the major mouthwash ingredients. The major ingredients are shown to table 2. Other less common ingredients include: zinc chloride, zinc citrate, sodium phosphate, zinc acetate, zinc lactate, zinc salicylate, zinc sulfate, zinc oxide, zinc gluconate, POE (20), POE (40), POE (60), menthol, pluronic F 108, lactodifucotetraose, urea peroxide, zinc tartarate, chlorhexidine gluconate, gluconolactone, tween 80, pluronic F-127, cetyl pyridinium chloride, isopropanol, propylene glycol, xanthan gum, benzthonium chloride, cremopher RH60, chlorphyillin, cocoamidopropylbetaine, NHDC, pluronic F-127 2, peppermint oil, tetraacetic acid, butylated hydroxyanisole, propyl paraben, and PEG 40.

TABLE 2

Mouthwash Ingredients

|  | Min % | Max % |
|---|---|---|
| Ecofriendly antimicrobials | 0.001 | 0.1 |
| 1 Water | 90 | 97 |
| 2 Other Ingredients | 0 | 4 |
| 3 Sodium lauryl Sulfate | 0.1 | 1 |
| 4 Color | 0 | 0.8 |
| 5 Sodium Chloride | 0.52 | 0.59 |
| 6 Sodium Citrate | 0.2 | 0.4 |
| 7 Sodium Benzoate | 0.1 | 0.3 |
| 8 Sodium Hydroxide | 0.02 | 0.27 |
| 9 Saccharin Sodium | 0.01 | 0.2 |
| 10 Methyl Paraben | 0.5 | 0.1 |
| 11 Sodium ricinoleate | 0.04 | 0.06 |

A number of implementations have been described. Nevertheless, it will be understood that additional modifications may be made without departing from the scope of the inventive concepts described herein, and, accordingly, other embodiments are within the scope of the following claims.

What is claimed is:

1. A skin and wound care device, comprising first and second microcrystallized or microencapsulated essential oils which are broad spectrum antimicrobials polymerized into a polymer.

2. The skin and wound care device of claim 1, wherein the first and second essential oils are microencapsulated into pectin shells.

3. The skin and wound care device of claim 2, wherein the microencapsulation takes place in a 1-10% pectin solution.

4. The skin and wound care device of claim 2, wherein the polymer comprises an alginate polymer.

5. The skin and wound care device of claim 2, wherein the polymer comprises a polyurethane foam.

6. The skin and wound care device of claim 1, wherein the polymer comprises cellulose.

7. The skin and wound care device of claim 6, wherein the cellulose comprises nanocrystalline or microcrystalline cellulose particles.

8. The skin and wound care device of claim 1, wherein the polymer comprises microcellulose, nanocellulose, alginate, polyurethane, collagen, hyaluronic acid, PEG, silicone, or a silicone acrylic polymer.

9. The skin and wound care device of claim 1, wherein the first and second microcrystallized or microencapsulated essential oils are mixed into a polymeric material comprising silicone, acrylic, nylon, polylactic acid, polyethylene, polypropylene, Teflon, polystyrene, polyurethane, alginate, PET, or PEEK.

10. The skin and wound care device of claim 1, comprising a rinse, gel, foam, wound dressing, suture, staple, or wipe.

11. The skin and wound care device of claim 1, wherein the first and second essential oils are microencapsulated in pectin shells.

12. The skin and wound care device of claim 11, wherein the first and second essential oils that are microencapsulated in pectin shells are polymerized into alginate polymer.

13. The skin and wound care device of claim 12, comprising a wound dressing.

14. The skin and wound care device of claim 1, wherein the first essential oil is cinnamon and the second essential oil is lemongrass.

15. A wound dressing, comprising: first and second essential oils which are broad spectrum antimicrobials microencapsulated into pectin shells, wherein the pectin shells are polymerized into an alginate polymer.

* * * * *